(12) United States Patent
Baldwin et al.

(10) Patent No.: US 7,700,545 B2
(45) Date of Patent: *Apr. 20, 2010

(54) USE OF NF-κB INHIBITION IN COMBINATION THERAPY FOR CANCER

(75) Inventors: Albert S. Baldwin, Chapel Hill, NC (US); James C. Cusack, Chapel Hill, NC (US); Marty W. Mayo, Durham, NC (US); Cun-Yu Wang, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/535,720

(22) Filed: Sep. 27, 2006

(65) Prior Publication Data

US 2007/0110828 A1 May 17, 2007

Related U.S. Application Data

(63) Continuation of application No. 10/979,402, filed on Nov. 2, 2004, which is a continuation of application No. 08/959,160, filed on Oct. 28, 1997, now Pat. No. 6,831,057.

(51) Int. Cl.
*A61K 38/00* (2006.01)
(52) U.S. Cl. .................................................. 514/2
(58) Field of Classification Search ................. None
See application file for complete search history.

(56) References Cited

U.S. PATENT DOCUMENTS

| 5,106,948 | A | * | 4/1992 | Kinder et al. ............... 530/331 |
| 5,532,388 | A | * | 7/1996 | Bouchard et al. ........... 549/510 |
| 5,550,262 | A | | 8/1996 | Iqbal et al. |
| 5,780,454 | A | | 7/1998 | Adams et al. |
| 6,054,467 | A | | 4/2000 | Gjerset |
| 6,297,217 | B1 | * | 10/2001 | Adams et al. ................ 514/18 |
| 6,410,516 | B1 | | 6/2002 | Baltimore et al. |
| 2001/0049349 | A1 | * | 12/2001 | Chinery et al. ................ 514/1 |

FOREIGN PATENT DOCUMENTS

| EP | 0 652 290 A1 | 10/1995 |
| WO | WO 90/12578 | 11/1990 |
| WO | WO 91-13904 | 9/1991 |
| WO | WO 92/20795 | 11/1992 |
| WO | WO 94/23045 | 10/1994 |
| WO | WO 95/01348 | 1/1995 |
| WO | WO 95-25533 | 9/1995 |
| WO | WO 9524914 A1 * | 9/1995 |
| WO | WO 96/10402 | 4/1996 |
| WO | WO 9613266 A1 * | 5/1996 |
| WO | WO 9625666 A1 * | 8/1996 |

OTHER PUBLICATIONS

Pusztai et al (J. Clinical Oncology vol. 21 (18) 2003 ).*
Cancer, Principles and Practice of oncology, 6th Edition Chappter 17, Lippincott Williams & Wilkins 1993, 289-306.*
K. Shinohara et al. Biochem. J. (1996) 317, pp. 385-388.*
N. Yamagishi et al. Int. J. Radiat. Biol. (1997) 72(2) , pp. 157-162.*
M. Higuchi et al. Blood. (1995) 86(6), pp. 2248-2256.*
Bentires-Alj et al. "Stable Inhibition of Nuclear Factor •B in Cancer Cells Does Not Increase Sensitivity to Cytotoxic Drugs" *Cancer Research* 59:811-815 (1999).
Branch, Andrea D. "A good antisense molecule is hard to find" *TIBS* 23:45-50 (1998).
Fox, Jeffrey L. "Investigation of gene therapy begins" *Nature Biotechnology* 18 143-144 (2000).
Gibbs et al "Pharmaceutical Research in Molecular Oncology" *Cell* 79:193-198 (1994).
Gura, Trisha "Systems for Identifying New Drugs Are Often Faulty" *Science* 278:1041-1042 (1997).
Krontiris "Molecular and Cellular Biology of Cancer" *Internal Medicine*, 4th Edition 699-715 (1995) by Stein et al. (Publisher: Mosby).
Orkin et al. "Report and Recommendations of the Panel to Assess the NIH Investment in Research on Gene Therapy" < www.nih.gov/news/panelrep.html> (2006).
Slater et al. "ConKomote apoptosis, but not inhibited by pyrrolidine dithiocarbamate" *Biochem. J.* 312:833-838 (1995).
Taglialatela et al. "Inhibition of Nuclear Factor Kappa B (NF•B) Activity Induces Nerve Growth Factor-Resistant Apoptosis in PC12 Cells" *Journal of Neuroscience Research* 47:155-162 (1997).
Verma et al. "Gene therapy—promises, problems and prospects" *Nature* 389:239-242 (1997).
Wang et al. "TNF- and Cancer Therapy-Induced Apoptosis: Potentiation by Inhibition of NF-•B" *Science* 274:784-787 (1996).

(Continued)

*Primary Examiner*—Andrew D Kosar
(74) *Attorney, Agent, or Firm*—Myers Bigel Sibley & Sajovec, P.A.

(57) ABSTRACT

The use of NF-κB inhibitors to enhance the cytotoxic effects of chemotherapy or radiation therapy in the treatment of neoplastic conditions is described.

22 Claims, 5 Drawing Sheets

OTHER PUBLICATIONS

Albert S. Baldwin, videotaped deposition, *Ariad Pharmaceuticals* v. *Eli Lilly*, pp. 262-274 and attachment A (Oct. 26, 2004).
Chabner B.A. and Roberts, Jr. T.G. Chemotherapy and the war on cancer. Nature Reviews. Jan. 2005. 5:65-72.
Lay J.D. et al. Sulfasalazine suppresses drug resistance and invasiveness of lung adenocarcinoma cells expressing AXL. Cancer Research. Apr. 15, 2007. 67(8):3878-87.
Lin Y.G. et al. Curcumin inhibits tumor growth and angiogenesis in ovarian carcinoma by targeting the nuclear factor-{kappa}B pathway. Clin Cancer Res. Jun. 1, 2007. 13(11):3423-30.
Kokura S. et al. The radical scavenger edaravone enhances the antitumor effects of CPT-11 in murine colon cancer by increasing apoptosis via inhibition of NF-kappaB. Cancer Lett. Nov. 18, 2005. 229(2): 223-33.
Ma M.H. et al. The proteasome inhibitor PS-341 markedly enhances sensitivity of multiple myeloma tumor cells to chemotherapeutic agents. Clinical Cancer Research. Mar. 2003. 9:1136-1144.
Aghajanian C. et al. Phase I trial of bortezomib and carboplatin in recurrent ovarian or primary peritoneal cancer. Journal of Clinical Oncology. Sep. 1, 2005. 23(25):5943-5949.
Mabuchi S. et al. Inhibition of inhibitor of nuclear factor-{kappa}B phosphorylation increases the efficacy of paclitaxel in in vitro and in vivo ovarian cancer models. Clinical Cancer Research. Nov. 15, 2004. 10:7645-7654.
Mabuchi S. et al. Inhibition of NF{kappa}B increases the efficacy of cisplatin in in vitro and in vivo ovarian cancer models. Journal of Biological Chemistry. May 28, 2004. 279(22):23477-23485.
Nakahara C. et al. Cyclosporin-A enhances docetaxel-induced apoptosis through inhibition of nuclear factor-{kappa}B activation in human gastric carcinoma cells. Clinical Cancer Research. Nov. 1, 2003. 9:5409-5416.
Cusack, Jr. J.C. et al. Inducible chemoresistance to 7-ethyl-10-[4-(1-piperidino)-1-piperidino]-carbonyloxycamptothecin (CPT-11) in colorectal cancer cells and a xenograft model is overcome by inhibition of nuclear factor-{kappa}B activation. Cancer Research. May 1, 2000. 60:2323-2330.
Mohammed R.M. et al. Genistein sensitizes diffuse large cell lymphoma to CHOP (cyclophosphamide, doxorubicin, vincristine, prednisone) chemotherapy. Molecular Cancer Therapeutics. 2003;2(12):1361-1368.
Sharma V. et al. Sensitization of cancer cells to DNA damaging agents by imidazolines. J. Am. Chem. Soc. 2006. 128:9137-9143.
Riggins R.B. et al. The nuclear factor {kappa}B inhibitor parthenolide restores ICI 182,780 (Faslodex; fulvestrant)-induced apoptosis in antiestrogen-resistant breast cancer cells. Molecular Cancer Therapeutics. Jan. 2005;4(1):33-41.
Wang C-Y. et al. Control of inducible chemoresistance: Enhanced anti-tumor therapy through increased apoptosis by inhibition of NF-{kappa}B. Apr. 1999. 5(4):412-417.
Ma C. et al. A phase I and pharmacologic study of sequences of the proteasome inhibitor, bortezomib (PS-341,Velcade™), in combination with paclitaxel and carboplatin in patients with advanced malignancies. Cancer Chemother Pharmacol. 2007. 59:207-215.
Cardosa F. et al. Bortezomib (PS-341, Velcade) increases the efficacy of trastuzumab (Herceptin) in HER-2-positive breast cancer cells in a synergistic manner. Molecular Cancer Therapeutics. Dec. 2006. 5(12):3042-3051.
Ludwig H. et al. Proteasome inhibition and its clinical prospects in the treatment of hematologic and solid malignancies. American Cancer Society. Sep. 21, 2005. 1794-1807.
Nencioni A. et al. Proteasome inhibitors: antitumor effects and beyond. Leukemia. 2007. 21:30-36.
Adams J. The development of proteasome inhibitors as anticancer drugs. Cancel Cell. May 2003. 5:417-421.
Zoli W. et al. In vitro preclinical models for a rational design of chemotherapy combinations in human tumors. Critical Reviews in Oncology/Hematology. 2001. 37:69-82.
Orkin et al. "Report and Recommendations of the Panel to Assess the NIH Investment in Research on Gene Therapy" < www.nih.gov/news/panelrep.html>, 1995, 36 pages.

Brown K et al. Control of IκB-α proteolysis by site-specific, signal-induced phosphorylation. Science. Mar. 10, 1995;267:1485-1488.
Palombella VJ et al. The ubiquitin-proteasome pathway is required for processing the NF-κB1 precursor protein and the activation of NF-κB. Cell. Sep. 9, 1994;78:773-785.
Wilkinson KD et al. A specific inhibitor of the ubiquitin activating enzyme: synthesis and characterization of adenosyl-phospho-ubiquitinol, a nonhydrolyzable ubiquitin adenylate analogue. Biochemistry. 1990;29(32):373-7380.
Dick LR et al. Degradation of oxidized insulin B chain by the multiproteinase complex macropain (proteasome). Biochemistry. 1991;30(10):2725-2734.
Goldberg A. The mechanism and functions of the ATP-dependent proteases in bacterial and animal cells. Eur. J. Biochem. 1992;203:9-23.
Orlowski M. The multicatalytic proteinase complex, a major extralysosomal proteolytic system. Biochemistry. Nov. 13, 1990;29(45):10289-10297.
Rivett AJ. The multicatalytic proteinase. Journal of Biological Chemistry. Jul. 25, 1989;264(21):12215-12219.
Li X et al. Isolation and characterization of a novel endogenous inhibitor of the proteasome. Biochemistry. 1991;30(40):9709-9715.
Vinitsky A et al. Inhibition of the chymotrypsin-like activity of the pituitary multicatalytic proteinase complex. Biochemistry. 1992;31(39):9421-9428.
Orlowski M et al. Evidence for the presence of five distinct proteolytic components in the pituitary multicatalytic proteinase complex. Properties of two components cleaving bonds on the carboxyl side of branched chain and small neutral amino acids. Biochemistry. 1993;32(6):1563-1572.
Odake S et al. Human and murine cytotoxic T lymphocyte serine proteases: subsite mapping with peptide thioester substrates and inhibition of enzyme activity and cytolysis by isocoumarins. Biochemistry. 1991;30(8):2217-2227.
Vijayalakshmi J et al. Structural study of porcine pancreatic elastase complexed with 7-amino-3-(2-bromoethoxy)-4-chloroisocoumarin as a nonreactivatable doubly covalent enzuyme-inhibitor complex. Biochemistry. 1991;30(8):2175-2183.
Powers JC et al. Reaction of porcine pancreatic elastase with 7-substituted 3-alkoxy-4-chloroisocoumarins: design of potent inhibitors using the crystal structure fot eh complex formed with 4-chloro-3-ethoxy-7-guanidinoisocoumarin. Biochemistry. 1990;19(12):3108-3118.
Sherman MP et al. Pyrrolidine dithiocarbamate inhibits induction of nitric oxide synthase activity in rat alveolar macrophages. Biochemical and Biophysical Research Communications. Mar. 31, 1993;191(3):1301-1308.
Scheinman RI et al. Role of transcriptional activation of IκBα in mediation of immunosuppression by glucocorticoids. Science. Oct. 13, 1995;270:283-286.
Auphan N et al. Immunosuppression by glucocorticoids: inhibition of NF_κB activity through induction of IκB synthesis. Science. Oct. 13, 1995;270:286-290.
Arlt A et al. Role of NF-kappaB and Akt/P13K in the resistance of pancreatic carcinoma cell lines against gemcitabine-induced cell death. Oncogene. May 2003 222;22(21):3243-51.
Wang W et al. Disulfiram-mediated inhibition of NF-kappaB activity enhances cytotoxicity of 5-fluoroacil in human colorectal cancer cell lines. Int J Cancer. Apr. 20, 2003;104(4):504-11.
Orlowski RZ et al. Randomized phase III study of pegylated liposomal doxorubicin plus bortezomib compared with bortezomib alone in relapsed or refractory multiple myeloma: combination therapy improves time to progression. J Clin Oncol. Sep. 1, 2007;25(25):3892-901.
Kunnumakkara AB et al. Curcumin potentiates antitumor activity of gemcitabine in an orthotopic model of pancreatic cancer through suppression of proliferation, angiogenesis, and inhibition of nuclear factor-kappaB-regulated gene products. Cancer Res. Apr. 15, 2007;67(8):3853-61.
Pham CG et al. Upregulation of Twist-1 by NF-kappaB blocks cytotoxicity induced by chemotherapeutic drugs. Mol Cell Biol, Jun. 2007;27(11):3920-35.

Fukuyama R et al. Role of IKK and oscillatory NFkappaB kinetics in MMP-9 gene expression and chemoresistance to 5-fluoroacil in RKO colorectal cancer cells. Mol Carcinog. May 2007;46(5):402-13.

Bhardwaj A et al. Resveratrol inhibits proliferation, induces apoptosis, and overcomes chemoresistance through down-regulation of STAT3 and nuclear factor-kappaB-regulated antiapoptotic and cell survival gene products in human multiple myeloma cells. Blood. Mar. 15, 2007;109(6):2293-302.

Sun C et al. Aurora kinase inhibition downregulates NF-κB and sensitizes tumour cells to chemotherapeutic agents. Biochemical and Biophysical Research Communications. Jan. 5, 2007;352(1):220-225.

Salvatore C et al. NF-kappaB activation contributes to anthracycline resistance pathway in human ovarian carcinoma cell line A2780. Int J Oncol. Sep. 2005;27(3):799-806.

Camp ER et al. Inducible nuclear factor-kappaB activation contributes to chemotherapy resistance in gastric cancer. J Am Coll Surg. Aug. 2004;199(2):249-58.

Voboril R et al. Inhibition of NF-kappaB augments sensitivity to 5-fluoroacil/folinic acid in colon cancer. J Surg Res. Aug. 2004;120(2):178-88.

Tapia MA et al. Inhibition of the canonical IKK/NF kappa B pathway sensitizes human cancer cells to doxorubicin. Cell Cycle. Jul. 2007;6(18):2284-92.

Romano MF et al. Rapamycin inhibits doxorubicin-induces NF-kappaB/Rel nuclear activity and enhances the apoptosis of melanoma cells. Eur J Cancer. Dec. 2004;40(18):2829-36.

Bottero V et al. Activatio of nuclear factor kappaB through the IKK complex by the topoisomerase poisons SN38 and doxorubicin: a brake to apoptosis in HeLa human carcinoma cells. Cancer Res. Nov. 1, 2001;61(21):7785-91.

Lagadec P et al. Pharmacological targeting of NF-kappaB potentiates the effect of the topoisomerase inhibitor CPT-11 on colon cancer cells. Br J Cancer. Jan. 29, 2008;98(2):335-44.

Dhandapani KM et al. Curcumin suppresses growth and chemoresistance of human glioblastoma cells via AP-1 and NFkappaB transcription factors. J Neurochem. Jul. 2007;102(2):522-38.

Notarbartolo M et al. Antitumor effects of curcumin, alone or in combination with cisplatin or doxorubicin, on human hepatic cancer cells. Analysis of their possible relationship to changes in NF-kB activation levels and in IAP gene expression. Cancer Lett. Jun. 16, 2005;224(1):53-65.

Shanmugam R et al. Restoring chemotherapy and hormone therapy sensitivity by parthenolide in a xenograft hormone refractory prostate cancer model. Prostate. Oct. 1, 2006;66(14):1498-511.

Sweeney CJ et al. The sesquiterpene lactone parthenolide in combination with docetaxel reduces metastasis and improves survival in a xenograft model of breast cancer. Mol Cancer Ther. Jun. 2005;4(6):1004-12.

Degraffenried LA et al. NF-kappa B inhibition markedly enhances sensitivity of resistant breast cancer cells to tomoxifen. Ann Oncol. Jun. 2004;15(6):885-90.

Venkatraman M et al. Biological and chemical inhibitors of NF-kappaB sensitize SiHa cells to cisplatin-induced apoptosis. Mol Carcinog. Sep. 2005;44(1):51-9.

* cited by examiner

USE OF NF-κB INHIBITION IN COMBINATION THERAPY FOR CANCER

This application is a continuation of U.S. patent application Ser. No. 10/979,403 filed Nov. 2, 2004, which in turn is a continuation of U.S. patent application Ser. No. 08/959,160, filed Oct. 28, 1997, now issued as U.S. Pat. No. 6,831,057, the disclosures of both of which are incorporated by reference herein in their entirety.

STATEMENT OF GOVERNMENT SUPPORT

This invention was made with government support under Grant Numbers AI35098 and 1F32-CA69790-01 from the National Institutes of Health and Grant Number DAMD17-94-J-4053 from the Department of the Army. The US Government has certain rights to this invention.

BACKGROUND OF THE INVENTION

The inducible transcription factor Nuclear Factor-kappa B (NF-κB) participates in the regulation of multiple cellular genes, including many involved in the immune and inflammatory processes (for example, GM-CSF, IL-6, IL-8 and IL-2). NF-κB is a member of the rel family of protein complexes, and is activated by cellular exposure to various factors, including phorbol 12-myristate 13-acetate (PMA), lipopolysaccharide (LPS), interleukin-1 (IL-1), tumor necrosis alpha (TNFα), and ultraviolet radiation. See Baldwin, *Annu. Rev. Immunol.* 14:649 (1996). NF-κB has also been implicated in the transcriptional activation of several viruses, including HIV-1 (Nabel et al., *Nature* 326:711 (1987); Kaufman et al., *Mol. Cell. Biol.*, 7:3759 (1987)). The various signaling pathways that can control the activation of NF-κB are not all clearly understood. It is apparent that different inducers can initiate their pathways through distinct receptors.

The latent cytoplasmic form of NF-κB is associated with a cytoplasmic inhibitory protein called IκB. Baeuerle and Baltimore, *Science* 242:540 (1988); PCT US92/04073 (WO 92/20795). The release of NF-κB from IκB results in the rapid appearance of the active form of NF-κB in the cell nucleus. Genes regulated by NF-κB can be transcriptionally activated minutes after exposure of the cell to the appropriate inducer. Activation of NF-κB after exposure of a cell to an inducer is correlated with the hyperphosphorylation of IκBα and its subsequent degradation. As IκB is diminished in the cytoplasm, NF-κB increases in the nucleus. Phosphorylation of IκB was once thought to lead to dissociation from NF-κB and subsequent proteolysis of IκB. Beg and Baldwin, *Genes Dev.* 7:2064 (1993). More recently, it has been proposed that the proteasome is responsible for signal-mediated degradation of IκBα and IκBβ. Baldwin, *Annu. Rev. Immunol.* 14:649 (1996). Phosphorylation of IκB apparently renders the molecule susceptible to proteolysis.

Activation of NF-κB has been suggested as playing a pathological role in the development of autoimmune diseases and chronic inflammatory diseases such as rheumatoid arthritis, and in acute situations such as septic shock.

SUMMARY OF THE INVENTION

A first aspect of the present invention is a method of enhancing the cytotoxic effects of an antineoplastic chemotherapeutic agent. A therapeutically effective amount of NF-κB inhibitor is administered in conjunction with the chemotherapeutic agent, so that the cytotoxic effect of the chemotherapeutic agent is increased compared to that which occurs in the absence of NF-κB inhibitor.

A further aspect of the present invention is a method of enhancing chemotherapeutic cytotoxicity in a subject treated with a chemotherapeutic agent. A therapeutically effective amount of NF-κB inhibitor is administered to a subject in conjunction with a chemotherapeutic agent. The cytotoxic effect of the chemotherapeutic agent is increased compared to that which occurs in the absence of NF-κB inhibitor.

A further aspect of the present invention is a method of enhancing the cytotoxic effect of TNFα, by administering a therapeutically effective amount of NF-κB inhibitor in conjunction with TNFα. The cytotoxic effect of TNFα is increased compared to that which occurs in the absence of NF-κB inhibitor.

A further aspect of the present invention is a method of enhancing chemotherapeutic cytotoxicity in a subject treated with TNFα, by administering a therapeutically effective amount of NF-κB inhibitor in conjunction with TNFα. The cytotoxic effect of TNFα is increased compared to that which occurs in the absence of NF-κB inhibitor.

A further aspect of the present invention is a method of screening a compound for the ability to reduce the anti-apoptotic protective effects of an NF-κB induced anti-apoptotic gene. A population of test cells is exposed to an anticancer treatment and a test compound, and the cell viability following the exposure is assessed. Reduced cell viability, compared to that which occurs in cells treated only with the anticancer treatment, indicates that the test compound reduces the anti-apoptotic effects of an NF-κB induced anti-apoptotic gene.

The foregoing and other objects and aspects of the present invention are explained in detail in the specification set forth below.

DETAILED DESCRIPTION

Figure 1A:
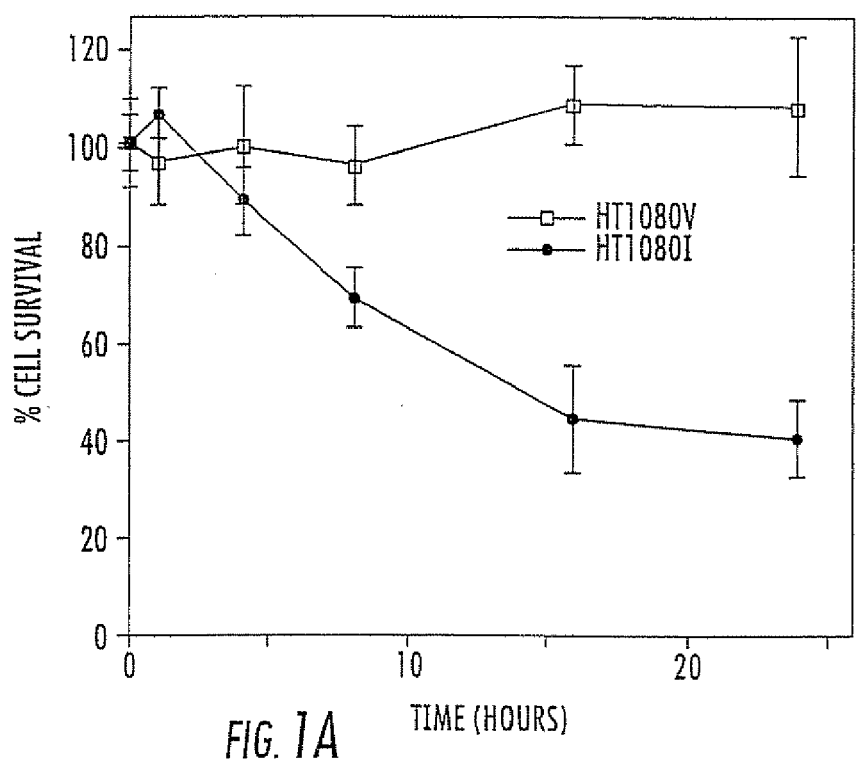
FIG. 1A graphs the percentage cell survival over time in fibrosarcoma cells expressing the super-repressor IκBα (HT1080I; solid diamonds) or in control fibrosarcoma cells containing the empty expression vector (HT1080V; open squares), after exposure to TNFα. (Data shown are the mean of three independent experiments ±SD and the percentage cell survival was defined as the relative number of THF treated versus untreated cells). TNF-mediated apoptosis was increased over time in cells expressing the super-repressor IκBα, compared to control cells.

Many cells are resistant to stimuli which are otherwise capable of inducing apoptosis, but the mechanisms involved are not fully understood. It is demonstrated herein that tumor necrosis factor (TNF), ionizing radiation, and anti-cancer chemotherapeutic compounds (such as daunorubicin), activate NF-κB and that this activation of NF-κB protects the cell against the cytotoxic effects of these treatments. By inhibiting NF-κB nuclear translocation, the present inventors enhanced the apoptotic killing achieved by these reagents; no such enhancement of apoptosis by NF-κB inhibitors was seen with apoptotic stimuli that do not activate NF-κB. These results indicate that NF-κB activation provides cellular resistance to killing by some apoptotic reagents, and provide a method to improve the efficacy of various cancer therapies.

Observations that NF-κB is activated by certain apoptotic stimuli suggests that this transcription factor plays a role in mediating aspects of programmed cell death. Baldwin, *Annu. Rev. Immunol.* 14:649 (1996); Verma et al., *Genes Dev.* 9:2723 (1995); Siebenlist et al., *Annu. Rev. Cell Biol.* 10:405 (1994); Liou and Baltimore, *Curr. Opin. Cell Biol.* 5:477 (1993); Baeuerle and Henkel, *Annu. Rev. Immunol.* 12:141 (1994). PCT patent application WO 97/30083 describes anti-apoptotic proteins capable of inhibiting NF-κB, and describes methods of decreasing apoptosis by administering such anti-apoptotic proteins. An anti-apoptotic function of NF-κB is also suggested by the finding that mice lacking the NF-κB p65/RelA gene die embryonically from extensive apoptosis within the liver. Beg et al., *Nature* 376:167 (1995). Furthermore, it has been observed that many cells which respond to TNF (a strong activator of NF-κB) are resistant to cell killing, and that TNF killing is enhanced in the presence of protein synthesis inhibitors. Holtmann et al., *Immunobiology* 177:7 (1988).

The present inventors investigated whether activation of NF-κB is protective against the apoptotic killing induced by TNF in a model cell system. Their studies used the human fibrosarcoma cell line HT1080 (which is relatively resistant to killing by TNF; Wang and Baldwin, unpublished data). In order to potentially block the activation of NF-κB in response to TNF stimulation, an HT1080 cell line (HT1080I) expressing a super-repressor form of the NF-κB inhibitor IκBα was established. The super-repressor IκBα contains serine to alanine mutations at residues 32 and 36, which inhibit signal-induced phosphorylation and which inhibit subsequent proteasome-mediated degradation of IκBα. This mutant IκBα protein acts as a super-repressor because it binds to NF-κB and inhibits DNA binding as well as nuclear translocation, but is unable to respond to cellular signals such as those induced by TNF. See Brockman et al., *Mol. Cell. Biol.* 15:2809 (1995); Brown et al., *Science* 267:1485 (1995); Traenckner et al., *EMBO J.* 14:2876 (1995); DiDonato et al., *Mol. Cell. Biol.* 16:1295 (1996); Palombello et al., *Cell* 78:773 (1994); Chen et al., *Genes Dev.* 9:1586(1995). A control line (HT1080V) was established that contained the empty vector and the hygromycin selectable marker. TNFα-induced NF-κB activation, as measured by DNA binding of nuclear extracts, was effectively blocked by the super-repressor IκBα in HT1080I cells as compared to the control cell line (see FIG. 3A).

Figure 1B:
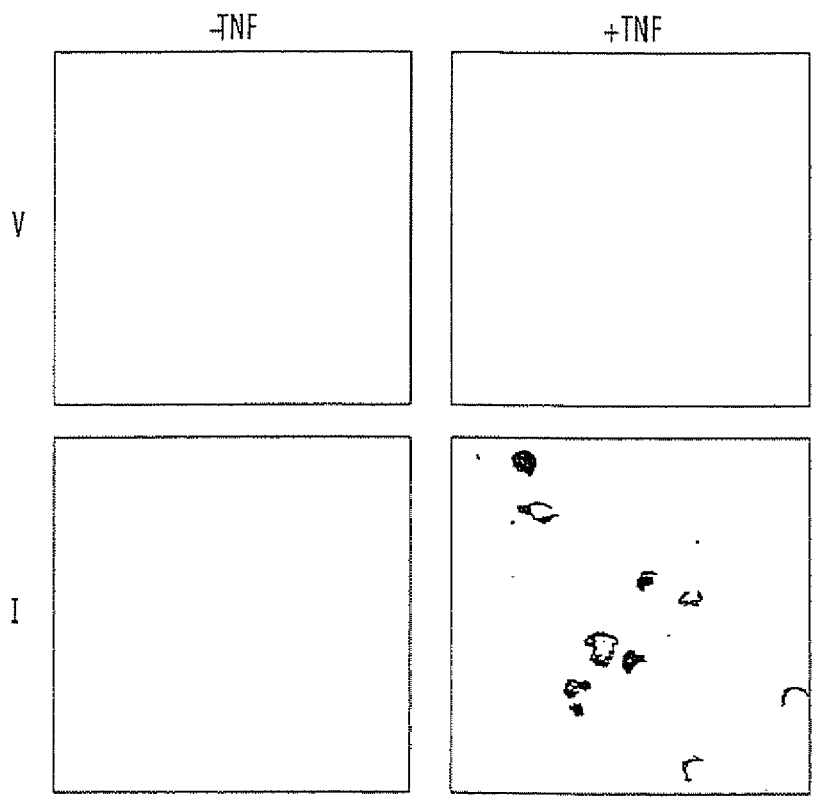
FIG. 1B portrays the detection of TNF-induced apoptosis by TUNEL staining in HT1080V (control; V) or HT1080I (super-repressor IκBα expressing; I) cells that were either untreated (−TNF) or stimulated (+TNF) with TNFα. Positive cells show the condensed morphology typical of apoptotic cells.

As shown in FIG. 1A, TNFα is much more effective at inducing apoptosis in the IκBα super-repressor expressing cells (HT1080I) than the control cell line (HT1080V). Similar results were obtained using pooled clones of HT1080V or HT1080I cells (data not shown), indicating that the results were due to overexpression of the super-repressor IκBα, and not to clonal variation. That cells were killed through apoptosis was confirmed by using the deoxynucleotidyl transferase-mediated dUTP nick end labeling (TUNEL) assay which measures DNA strand breaks and is therefore diagnostic for cells undergoing apoptosis. Apoptosis was observed only in the HT1080I cells treated with TNF (FIG. 1B). Thus, expression of a super-repressor form of IκBα, known to be highly effective at inhibiting NF-κB nuclear translocation, was found to enhance the ability of TNF to initiate apoptosis in cells that are normally resistant to this cytokine. These data indicate, therefore, that the activation of NF-κB by TNF is protective, providing protection against the cell killing induced by this apoptotic agent.

Figure 2A:
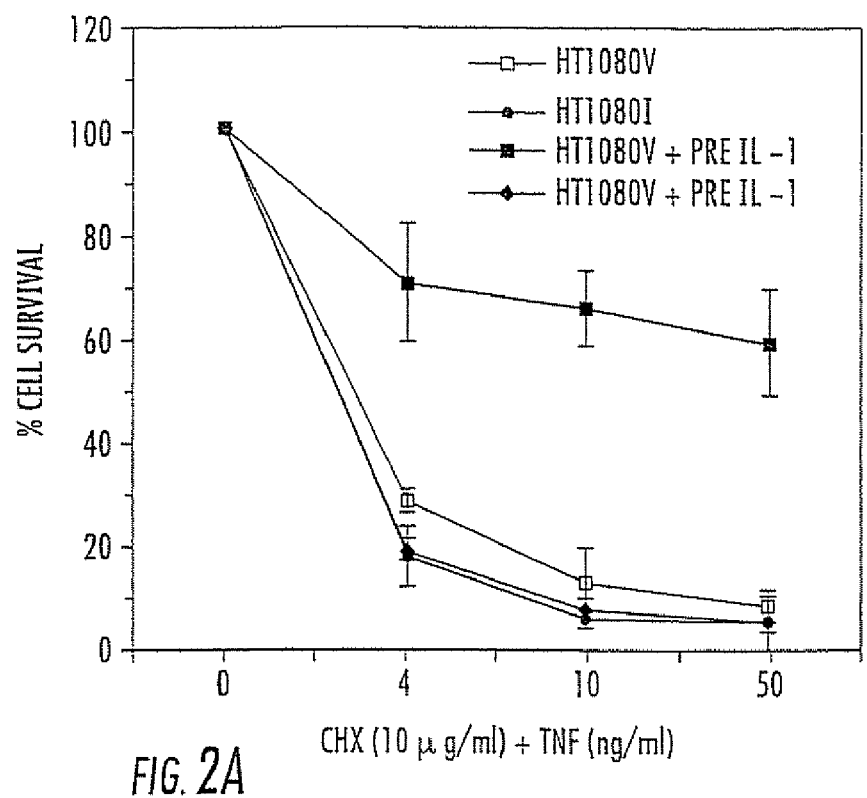
FIG. 2A graphs cell survival over time in HT1080V (control) or HT1080I (super-repressor IκBα expressing) cells pretreated with IL-1 prior to exposure to TNFα and CHX. Interleukin-1 (IL-1) pre-treatment inhibited TNFα+CHX-induced apoptosis in HT1080V cells. Open squares represent HT1080V cells without IL-1 pretreatment; closed squares represent HT1080V cells pretreated with IL-1; circles represent HT1080I cells without IL-1 pretreatment; triangles represent HT1080I cells pretreated with IL-1.

To exclude the possibility that the expression of the super-repressor form of IκBα leads to a function that is different from the inhibition of NF-κB, the present inventors confirmed the requirement for NF-κB in the inhibition of TNF-induced apoptosis. The pre-treatment of HT1080V cells (control cells) with interleukin-1 (IL-1, an activator of NF-κB that does not initiate apoptosis) blocked the subsequent killing of these cells induced by combined cycloheximide (CHX) and TNF treatment. As shown in FIG. 2A, IL-1 pre-treatment of the HT1080V cells protected against CHX+TNF-induced killing, compared to cells which were not pretreated. As a control and to show that it was NF-κB that was responsible for the protection against apoptosis, it was demonstrated that IL-1 had no protective effect on the HT1080I cell line, in which NF-κB activation is blocked by the expression of the super-repressor IκB α (FIG. 2A). Holtmann et al. reported that IL-1 pretreatment was capable of blocking TNF-mediated killing (*Immunobiology* 177:7 (1988)). The present inventors' results indicate that the mechanism behind the ability of IL-1 to inhibit TNT-responsive apoptosis is the induction of NF-κB.

The present inventors additionally determined that proteasome inhibitors enhanced cell killing of HT1080 cells in response to TNF treatment. The degradation of IκB that results in the release of active NF-κB is controlled by the proteasome following inducible phosphorylation and subsequent ubiquitination of IκB (Palombello et al., *Cell* 78:773 (1994); Chen et al., *Genes Dev.* 9:1586(1995)). Proteasome inhibitors of the peptide aldehyde category are potent inhibitors of NF-κB activation (Palombello et al., *Cell* 78:773 (1994); Chen et al., *Genes Dev.* 9:1586(1995)). The present inventors demonstrated that, in a dose-dependent fashion, the proteasome inhibitor MG132 (Z-leu-leu-leu-H) strongly enhanced the killing of HT1080V cells in response to TNF (data not shown).

Figure 2B:
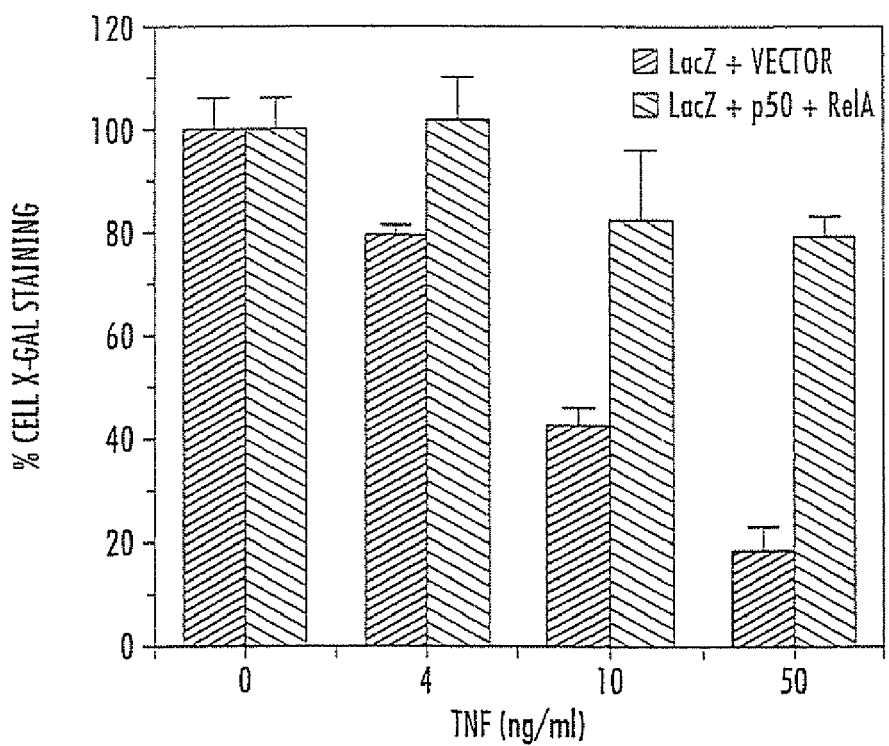
FIG. 2B compares the extent of TNFα-induced apoptosis in HT1080I cells (expressing the super-repressor IκBα) co-transfected to express LacZ, p65 and p50 (hatched bars) or co-transfected with the LacZ and empty vectors. After 40 hours, cells were treated with different concentrations of TNFα for an additional 24 hours. (Results are from the mean±SD of two experiments). Expression of the p50 and RelA/p65 NH-κB subunits restored cell resistance to TNFα-induced apoptosis in cells expressing the super-repressor IκBα.

If NF-κB inhibition sensitizes cells to TNF killing, then overexpression of NF-κB subunits should restore protection against cell killing in the present HT1080I model. Vectors encoding the p50 and RelA/p65 subunits of NF-κB or the empty CMV vector control were transfected into the HT1080I cells, and the cells were stimulated with TNF. As expected, the vector alone did not provide protection against cell killing induced by TNF (FIG. 2B). However, expression of the NF-κB p50 and RelA/p65 subunits provided protection against TNF-induced apoptosis, indicating that it is NF-κB that is blocked by the super-repressor IκBα, and that NF-κB expression blocks programmed cell death. Additional evidence that NF-κB is required for protection against TNF-induced apoptosis is shown by the fact that embryonic fibroblasts from RelA/p65 null mice (Beg et al., *Nature* 376:167 (1995)) are killed by TNF with a much higher frequency than those from wild-type animals (data not shown; see also Beg and Baltimore, *Science* 274:782 (1996)).

Slater et al. reported that in thymocytes (which constitutively express NF-κB) the intensity of the NF-κB/rel protein-DNA complex was enhanced after exposure to etoposide (an agent known to induce apoptosis in thymocytes). Slater et al., *Biochem J.* 312:844 (1995). These authors concluded that NF-κB expression is correlated with subsequent apoptosis. Bessho et al. examined the effect of pyrrolidine dithiocarbamate (PDTC) on the induction of apoptosis by a variety of agents. Bessho et al., *Biochem, Pharm.* 48:1883 (1994). They reported that treatment of a human promyelocytic leukemia cell line with etoposide or 1-beta-D-arabinofaranosylcytosine induced NF-κB activation, with apoptosis occurring in 3-4 hours. Addition of PDTC was reported to block NF-κB activation; these authors concluded that etoposide- and dexamethasone-induced apoptosis in human thymocytes was also blocked by PDTC, and that the activation of NF-κB plays a role in the apoptotic process of human hematopoietic cells.

Figure 3A:
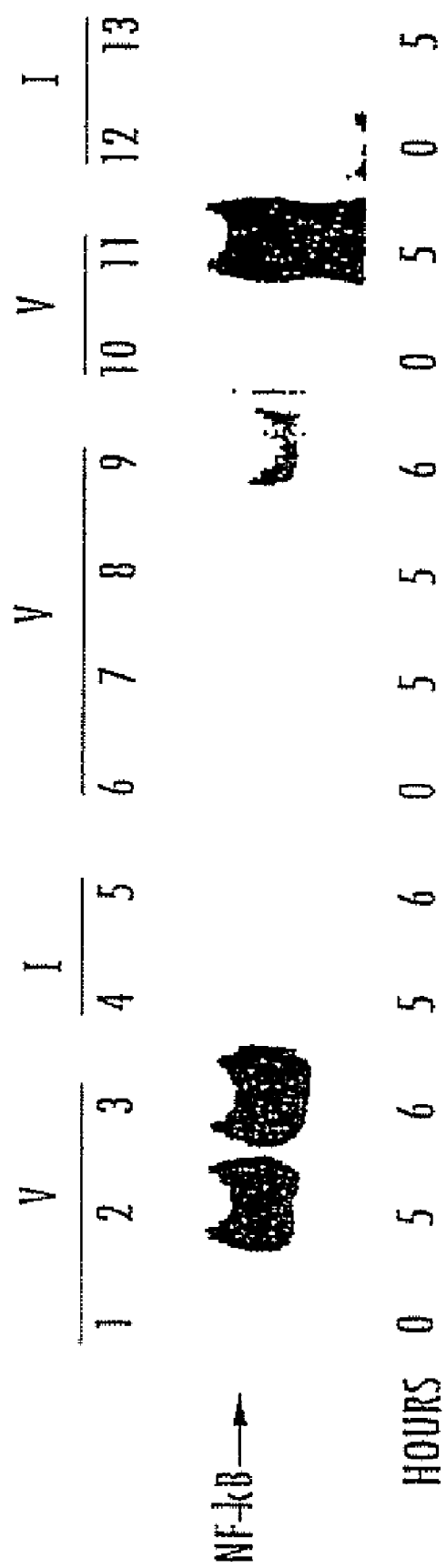
FIG. 3A provides the results of electrophoretic mobility-shift assays (EMSA) that indicate NF-κB nuclear translocation. HT1080V (control; V) or HT1080I (expressing the super-repressor IκBα; I) cells were treated with daunorubicin, staurosporine, or irradiation. (Lanes 1-5, daunorubicin; Lanes 6-9, staurosporine; and Lanes 10-13, ionizing radiation). In HT1080V control cells, both daunorubicin (lanes 1-3) and ionzing radiation (lanes 10-11) activated NF-κB and resulted in nuclear translocation over time. In contrast, activation of NF-κB by daunorubicin and ionizing radiation was blocked in HT1080I cells (lanes 4-5 and 12-13, respectively). Treatment with staurosporine did not result in NF-κB nuclear translocation in HT1080V control cells (lanes 6-9).

Many cancer therapies function to kill neoplastic cells through apoptotic mechanisms; cellular resistance to apoptosis provides protection against cytotoxic therapies (reviewed in Fisher, *Cell*, 78:539 (1994)). To determine if other apoptotic stimuli in addition to TNF activate NF-κB and induce a protective effect of NF-κB, the present inventors analyzed ionizing radiation-, daunorubicin- and staurosporine-treated cells. Ionizing radiation has been shown to activate NF-κB in several cell types (Singh and Lavin, *Mol. Cell. Biol.* 10:5279 (1990); Brach et al., *J. Clin. Invest.* 88:691 (1991)). The present inventors first investigated whether ionizing radiation, the chemotherapeutic compound daunorubicin, or staurosporine activated NF-κB in the HT1080V cells and in the HT1080I cells. Data shown in FIG. 3A shows that both daunorubicin (lanes 1-3) and ionizing radiation (lanes 10-11) activated NF-κB. Importantly, the ability of these two stimuli to activate NF-κB in HT1080I cells (expressing the super-repressor IκBα) was blocked (FIG. 3A, lines 4-5 and lane 13). In contrast, staurosporine (a cytotoxic agent that is not used in cancer treatment) did not activate NF-κB (FIG. 3A, lanes 6-9).

The present inventors also tested whether ionizing radiation-, daunorubicin-, and staurosporine-induced cell killing could be enhanced by the inhibition of NF-κB activity. Daunorubicin (FIG. 3B) and ionizing radiation (FIG. 3C) were found to induce NF-κB activation; the cytotoxicity of these agents was enhanced in HT1080I cells (expressing the super-repressor IκBα) compared to control cells. However, apoptosis induced by staurosporine was not enhanced by the expression of IκBα. (data not shown), consistent with the present inventors' observation that staurosporine does not effectively activate NF-κB (FIG. 3A). Thus, the activation of NF-κB is part of the cellular response to a variety of cytotoxic agents, and provides protection against the apoptosis caused by such agents. The present inventors data additionally indicate that cell killing by vincristine is augmented by the inhibition of NF-κB (data not shown). Tumor growth after treatment with the antineoplastic CPT-11 (irinotecan), with and without the adenoviral delivery of the super-repressor IκB, was also studied. CPT-11 activated NF-κB (data not shown). Tumors receiving both IκB and CPT-11 showed essentially no growth during the 20 days after treatment (FIG. 4); cytotoxicity of the chemotherapeutic agent was increased when combined with the super-repressor IκB. Cell-killing was by apoptosis (data not shown).

The present data indicate that the activation of NF-κB by TNF, ionizing radiation, and chemotherapeutic agents (such as daunorubicin, vincristine and irinotecan) protects cells against the apoptotic cell killing induced by these stimuli. Distinct signaling pathways initiated by TNF engagement of its receptor lead to activation of both apoptosis and NF-κB, and NF-κB does not play a positive role in the induction of apoptosis (Tartaglia and Goeddel, *Immunol. Today* 13:151 (1992); Vandenabeele et al., *Trends Cell. Biol.* 5:392 (1995); Hsu et al., *Cell* 81:495 (1995); Hsu et al., *Cell* 84:299 (1996); Chinnaiyan et al., *Cell* 81:505 (1995); Goncharov et al., *Cell* 84:803 (1996); Hsu et al., *Immunity* 4:387 (1996)). In the case of ionizing radiation and daunorubicin the activation of apoptosis appears to be initiated by ceramide production (Bose et al., *Cell* 82:405 (1992); Jaffezou et al., *EMBO J.* 15:2417 (1996); Haimovitz-Freedman et al., *J. Exp. Med.* 180:525 (1994); Santana et al., *Cell* 86:189 (1996)), and the cytotoxic effects of TNF have been reported to require ceramide activation (Kolesnick and Golde, *Cell* 77:325 (1994)). Ceramide alone has been shown to lead to apoptosis (Obeid et al., *Science* 259:1769 (1993)) but the details of this apoptotic pathway are not fully understood. It should be noted that several groups have suggested that NF-κB may function pro-apoptotically under some conditions and in certain cell lines (Jung et al *Science* 268:1619 (1995); Lin et al., *J. Cell Biol.* 131:1149 (1995); Grimm et al., *J. Cell Biol.* 134:1 (1996)).

Growing evidence indicates that a variety of anticancer agents kill through programmed cell death. Resistance to anticancer therapies appears to be mediated by resistance to apoptosis (Fisher, *Cell* 78:539 (1994)). The present data demonstrate that several anticancer agents may be less effective at inducing programmed cell death because of their concomitant activation of NF-κB.

As used herein, "NF-κB activation" refers to NF-κB-mediated up-regulation of genes which are directly or indirectly under the control of an NF-κB binding site. In functional terms, NF-κB activation comprises the binding of NF-κB to κB regulatory sequences in the DNA of a cell, so that transcription of the operatively associated gene is induced (other factors acting in combination with NF-κB may be required to initiate transcription).

"NF-κB inhibition" refers to the prevention of NF-κB binding to NF-κB binding sites in nuclear DNA. NF-κB inhibition does not necessarily imply that all NF-κB-induced transcription is prevented, but rather that such transcription occurs at levels substantially less than that which would occur in the absence of NF-κB inhibition. For example, NF-κB inhibition may result in a 30% reduction in NF-κB-induced transcription of a gene, more preferably a 40%, 50%, or 60% reduction in NF-κB-induced transcription of a gene, and even more preferably a 70%, 80%, 90%, 95% or greater reduction in NF-κB-induced transcription of a gene.

An "NF-κB inhibiting substance", "NF-κB inhibitor", or "NF-κB induction inhibitor" refers to a substance capable of preventing or reducing NF-κB binding to NF-κB binding sites in nuclear DNA, compared to that which would occur in the absence of the NF-κB inhibiting substance.

According to the present invention, methods or compounds that inhibit activation or nuclear translocation of NF-κB, are utilized to enhance the cellular apoptosis caused by various anti-cancer therapies. Methods according to the present invention include treatment of a subject by the administration of an NF-κB inhibitor in conjunction with an anti-cancer therapy, where the anti-cancer therapy alone would induce the anti-apoptotic effects of NF-κB. Addition of the NF-κB inhibitor permits or enhances the apoptotic cell-killing effects of the anti-cancer therapy. Such combined therapy is useful in the treatment of tumors and other neoplastic growths and conditions. Thus, combined therapy that inhibits NF-κB function in the presence of apoptotic stimuli lowers the apoptotic threshold of neoplastic cells and provides a more effective treatment against resistant forms of cancer. Additionally, the inhibition of NF-κB function in association with TNF treatment enhances the previously limited usefulness of this cytokine as an anti-tumor agent.

Methods of the present invention comprise the co-administration of an anti-cancer agent or treatment that induces NF-κB activation, and an NF-κB inhibitor. Such concurrent therapy enhances the cytotoxic ability of the anti-cancer agent, compared to that which would occur in the absence of NF-κB inhibitor. Any suitable NF-κB inhibitor or method of inhibiting NF-κB activation may be used in the present methods. One such method of inhibition is the delivery of the super-repressor IκBα to cells undergoing anti-cancer treatment, including via delivery of nucleotide sequences encoding the super-repressor IκBα. A variety of agents (examples discussed below) are known as NF-κB inhibitors, including proteasome inhibitors, inhibitors of ubiquitin conjugation, inhibitors of proteasome peptidases, and protease inhibitors. Additionally, the use of antisense oligonucleotides to control the expression of cellular components is known in the art, and may be utilized in the present methods to reduce the expression of NFκB or its subunits. (Antisense oligonucleotides that hybridize to NF-κB mRNA, and their therapeutic use to suppress processes that depend on activation of NF-κB, are described in WO95/35032).

One proteolytic pathway in the cytosol involves the covalent conjugation of cellular proteins with the ubiquitin polypeptide (see, e.g., Hiershko et al., *Ann. Rev. Biochem.* 61:761 (1992)). The conjugated proteins are then hydrolyzed by a proteolytic complex containing a degradative particle called the proteasome (Goldberg et al, *Nature*, 357:375 (1992)). The proteasome is composed of multiple subunits and contains at least three different peptidases (Goldberg et al., *Nature* 357:375 (1992); Goldberg, *Eur. J. Biochem.* 203:9 (1992); Orlowski, *Biochemistry* 29:10289 (1990); Rivett et al., *Arch. Biochem. Biophys.* 218:1 (1989); Tanaka et al., *New Biol.* 4:1 (1992)). These peptidases are referred to as chymotrypsin-like peptidase, the trypsin-like peptidase, and the peptidylglutamyl peptidase.

WO 95/25533 describes a method of reducing the cellular content and activity of NF-κB by contacting cells with inhibitors of proteasome function or ubiquitin conjugation; inhibition of proteolysis is achieved by interfering with the ubiquitin dependent pathway at any of several possible steps (e.g., interfering with the activity of the proteasome complex, or interfering with the activity of a proteasome component). Various inhibitors of ubiquitin conjugation to proteins are also known (Wilkinson et al., *Biochemistry* 29:7373 (1990)).

Various inhibitors of the peptidases of the proteasome have been reported (Dick et al., *Biochemistry* 30:2725 (1991); Goldberg et al., *Nature* 357:375 (1992); Goldberg, *Eur. J. Biochem.* 203:9 (1992); Orlowski, *Biochemistry* 29:10289 (1990); Rivett et al., *Arch. Biochem. Biophys.* 218:1 (1989); Rivett et al., *J. Biol. Chem.* 264:12215 (1989); Tanaka et al., *New Biol.* 4:1 (1992)). These inhibitors include known inhibitors of chymotrypsin-like and trypsin-like proteases, and inhibitors of thiol (or cysteine) and serine proteases. Some endogenous inhibitors of proteasome activities have also been isolated (Murakami et al., *Proc. Natl. Acad. Sci. USA* 83:7588 (1986); Li et al., *Biochemistry* 30:9709 (1991); Golberg, *Eur. J. Biochem.* 203:9 (1992); Aoyagi et al., *Proteases and Biological Control*, Cold Spring Harbor Laboratory Press, pp. 429 (1975); Siman et al., WO 91/13904). Potential inhibitors of the chymotrypsin-like activity of the proteasome have been tested (Vinitsky et al., *Biochemistry* 31:9421 (1992); Orlowski et al. *Biochemistry* 32:1563-1572 (1993); see also WO 95/25533).

Natural and chemical protease inhibitors include peptides containing an α-diketone or an α-keto ester, peptide chloromethyl ketones, isocoumarins, peptide sulfonyl fluorides, peptidyl boronates, peptide epoxides, and peptidyl diazomethanes (see e.g., Angelastro et al., *J. Med. Chem.* 33:11 (1990); Bey et al., EPO 363,284; Bey et al., EPO 364,344; Grubb et al., WO 88/10266; Higuchi et al., EPO 393,457; Ewoldt et al., Molecular Immunology 29:713 (1992); Hernandez et al., *J. Medicinal Chem.* 35:1121 (1992); Vlasak et al, *J. Virology* 63:2056 (1989); Hudig et al., *J. Immunology* 147:1360 (1991); Odake et al, *Biochemistry* 30:2217 (1991); Vijayalakshmi et al., *Biochemistry* 30:2217 (1991); Kam et al., *Thrombosis and Haemostasis* 64:133 (1990); Powers et al., *J. Cell. Biochem.* 39:33 (1989); Powers et al., *Proteinase Inhibitors*, Barrett et al. (Eds.), Elsevier, pp. 55-152 (1986); Powers et al., *Biochemistry* 29:3108 (1990); Oweida et al., *Thrombosis Research* 58:391 (1990)).

Sherman et al. report that pyrrolidine dithiocarbamate (PDTC) is an inhibitor of NF-κB activation. Sherman et al., *Biochem. Biophys. Res. Comm.* 191:1301 (1993). Anti-inflammatory steroids are suggested as NF-κB induction inhibitors in PCT/US95/12534 (WO/96/10402), including but not limited to predonsone, prednisolone, methyl prednisolone, dexamethasone, predisone, deoxycorticosterone, cortisone, hydrocortisone. Nonglucocorticoid lazaroids are also suggested for use as NF-κB induction inhibitors. Novel amides that are inhibitors of NF-κB DNA binding are described in WO 97/23457. Japanese patent applications JP 7291859 and JP 7291860 describe chemical inhibitors of NF-κB activity. Additional compounds stated to be useful for inhibiting the action of NF-κB in the nucleus are provided in WO 95/01348. Antisense oligonucleotides that hybridize to NF-κB mRNA, and their therapeutic use to suppress processes which depend on activation of NF-κB, is described in WO95/35032.

The administration of an NF-κB inhibitor to neoplastic cells according to the present invention may also be accomplished by gene therapy, e.g., by transfecting a cell to be treated with a nucleic acid sequence encoding an NF-κB inhibitor. The sequence may be incorporated, according to standard methods, into a mammalian vector suitable for transfecting mammalian cells in vivo, such as an adenovirus, a modified vaccinia virus, an Epstein Barr virus, or the like. The use of retroviral vectors particularly replication-defective retroviral vectors) for gene delivery is well-known in the art and may be used to transform cells for treatment according to the present invention. Alternative methods of targeted gene delivery include DNA-protein conjugates, liposomes, and other methods as are known in the art.

Methods for introducing genes into mammalian cells are known in the art. In the present methods, the vector is introduced to the subject, preferably by direct administration (such as by injection) to the tumor or area to be treated. It is appreciated that the vector may be introduced into nearby non-target cells as well as the target cells when the vector is injected into the treatment area.

Glucocorticoids are widely used as immune and inflammatory suppressants, and inhibit NF-κB (Ray and Prefontaine, *Proc. Natl. Acad. Sci. USA* 91:752 (1994); Mukaida et al., *J. Biol. Chem.* 269:13289 (1994); Scheinrnan et al., *Mol. Cell Biol.* 15:943 (1995); Caldenhoven et al., *Mol. Endocrinol.* 9:401 (1995); Scheinman et al., *Science* 270:283 (1995); Auphan et al, *Science* 270:286 (1995)). Glucocorticoids are presently used as part of a therapy for certain hematological malignancies (DeVita et al., *Cancer Res*, 47:5810 (1987); Schartzman and Cidlowski, *Endocrinol. Rev.* 14:133 (1993)).

NF-κB inhibitors used according to the methods of the present invention may be administered by any suitable means, as would be apparent to one skilled in the art, including systemically (e.g., intravenously) or locally (e.g., injected into a tumor, a tumor cyst, tissues immediately surrounding a tumor, or into an anatomic compartment containing a tumor). For example, where a therapeutically effective amount of NF-κB is utilized as an adjunct to chemotherapy, the NF-κB may be administered locally to a tumor or neoplasm (or the immediately surrounding tissue). Where a chemotherapeutic agent is delivered systemically, for example, a therapeutically effective amount of NF-κB inhibitor may be administered systemically by intravenous injection. Alternatively, the NF-κB inhibitor may be administered by a route different than that used for the chemotherapeutic agent (e.g., local administration of NF-κB inhibitor to a tumor combined with systemic administration of a chemotherapeutic agent).

The present inventors have determined that anti-cancer treatments can activate NF-κB, and that this activation of NF-κB suppresses apoptosis. The co-administration of NF-κB inhibitors with an anti-cancer treatment, to enhance the apoptotic effects achieved by the cancer treatment, is an aspect of the present invention.

A further aspect of the present invention is a screening assay to identity compounds that inhibit NF-κB induced anti-apoptotic genes (i.e., genes that are induced by NF-κB and that increase the resistance of the cell to apoptotic stimuli, and more specifically, increase the resistance of the cell to the apoptotic effects of an anti-cancer treatment). Such a screening method may comprise exposing a population of test cells to both an anti-cancer treatment and a test compound, and determining cell viability after such exposure. Reduced cell viability or reduced cell survival in the test cells (compared to that which occurs or would be expected to occur after treatment with the anti-cancer treatment alone) indicates that the test compound is capable of inhibiting the anti-apoptotic effects of a gene that is controlled by NF-κB. (The test compound may first be screened to document that it is not an inhibitor of NF-κB activation; any observed reduction in cell survival would thus not be due to inhibition of NF-κB activation, but to effects on the NF-κB induced gene itself.)

A further aspect of the present invention is a method of identifying NF-κB induced genes, including those that have an anti-apoptotic effect. Such a method utilizes techniques known in the art for constructing a cDNA library of a cell, such as polymerase chain reaction (PCR). (See, e.g., U.S. Pat. No. 5,589,622 to Gurr et al.) The cDNA library of a cell exposed to an anticancer therapy that is known to activate the anti-apoptotic effects of NF-κB is compared to the cDNA library of a control cell that was not exposed to the anticancer treatment. cDNA clones representing genes that are induced by activated NF-κB are then identified. The cDNA clones may then be used to isolate the corresponding genomic clone.

Genes induced by NF-κB that suppress apoptosis (i.e, have anti-apoptotic effects) can be used in screening assays to identify compounds that inhibit the anti-apoptotic effects of the genes. Such a method would comprise comparing cells exposed to activated NF-κB and test compound, and cells that were exposed to activated NF-κB only. Compounds that reduce or prevent the anti-apoptotic effects of the identified gene may be useful in enhancing the cytotoxic effects of anticancer therapies, or be useful as anticancer agents themselves.

Thus a further method of the present invention is the co-administration of an anti-cancer treatment with a compound that reduces or prevents the effects of an NF-κB-induced anti-apoptotic gene. Such a compound may act to prevent transcription or translation of the anti-apoptotic gene, or interact with the gene product.

The present invention also provides pharmaceutical compositions for use in the treatment of cancer and neoplastic diseases. The preferred embodiment compositions comprise mixtures of an antineoplastic agent and a suitable NF-κB inhibitor, with suitable pharmaceutical carriers and diluents. Thus, a preferred embodiment composition comprises: (a) an effective amount of an NF-κB inhibitor and (b) an effective amount of a chemotherapeutic agent.

Pharmaceutical compositions in accordance with the present invention may be administered by any suitable means, as would be apparent to one of ordinary skill in the art, including orally (in the form of tablets, capsules or solutions), or parenterally (in the form of injections or pellets). Such preparations can be made using known pharmaceutically accepted carriers and excipients. For administration, the compositions of the present invention will generally be mixed, prior to administration, with a non-toxic pharmaceutically acceptable carrier substance (e.g., normal saline or phosphate-buffered saline), and may be administered using any medically appropriate procedure including oral, intravenous, intraarterial, intradermal, intracavity and intrathecal administration, and direct injection into the tissue to be treated.

Subjects suitable for treatment according to the present invention are preferably mammals, and include humans, non-human primates, and non-primate mammals (including veterinary and livestock subjects), that suffer from a neoplastic disease or tumor, including but not limited to lung, breast, prostate, brain, kidney, liver, spleen, pancreas, bone and muscle cancers. Subjects may have solid or cystic tumors, or diffuse disease.

The methods disclosed herein may be used in subjects having solid or cystic tumors, such as brain tumors or tumors residing in other solid organs. Treatment may comprise administration of NF-κB inhibitors to the tissue of a solid tumor or to the cystic cavity of a cystic tumor (that is, a tumor surrounding a fluid-filled cavity), or may comprise surgical removal of the solid tumor with administration of NF-κB inhibitor to the resection cavity created by the surgery. Administration of NF-κB inhibitors according to the present invention is in conjunction with chemotherapy or radiation therapy suitable for treatment of the target neoplasm.

Any type of cancer, tumor or neoplasia (both benign and malignant) may be treated by the methods of the present invention, including sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

According to the present invention, NF-κB inhibitors are utilized as adjuncts in the chemotherapy or radiotherapy of neoplastic disease. The NF-κB inhibitor is provided in a therapeutically effective amount (i.e., an amount sufficient to increase or enhance the cytotoxic effectiveness of the co-administered chemotherapeutic agent or radiation treatment), compared to that which would occur in the absence of NF-κB inhibitor. The use of NFκB inhibitors according to the present method enhances the cytotoxic effects of cancer therapies by preventing activation of NF-κB, thus preventing the protective (anti-apoptotic) effects of NF-κB. Cytotoxicity may be assessed by a reduction in the proliferation of cells and/or decreased numbers of viable cells, leading to a total decrease in the number of viable cells.

As used herein, a therapeutically effective amount of an NF-κB inhibitor refers to those dosages or amounts which decrease or prevent the activation of NF-κB such that the treated cell, or treated population of cells, is more susceptible to the apoptotic effects of a cytotoxic chemotherapy or radiation therapy. Increased susceptibility of cells may be evidenced by decreased cell survival compared to control cells treated without the co-administration of an NF-κB inhibitor; or by the ability to decrease the dosage of the co-administered chemotherapeutic agent or radiation treatment, compared to the dosage required in control cells treated without co-administered NF-κB. Effective dosages of NF-κB inhibitors according to the present invention may vary depending upon the specific NF-κB inhibitor used, the time of administration, the condition being treated, the route of administration, the co-administered cytotoxic agent, and the general condition of the subject being treated. In vitro and animal models to determine particular effective dosages are available and apparent to those of skill in the art. The use of NF-κB inhibiting agents to enhance the cytotoxicity of agents used in the treatment of neoplastic cell growth will be a useful adjunct in treating tumors, cancers, and other neoplastic conditions.

Suitable dosages of NF-κB inhibitors will vary as discussed above, but may range from about 0.001 mg/kg, 0.01 mg/kg, 0.1 mg/kg or 0.3 mg/kg; to about 0.3 mg/kg, 0.5 mg/kg, 1.0 mg/kg, or 10.0 mg/kg, or more.

As used herein, the term chemotherapeutic agent refers to cytotoxic antineoplastic agents, that is, chemical agents which preferentially kill neoplastic cells or disrupt the cell cycle of rapidly proliferating cells, used therapeutically to prevent or reduce the growth of neoplastic cells. Chemotherapeutic agents are also known as antineoplastic drugs or cytotoxic agents, and are well known in the art. As used herein, chemotherapy includes treatment with a single chemotherapeutic agent or with a combination of agents. In a subject in need of treatment, chemotherapy may be combined with surgical treatment or radiation therapy, or with other antineoplastic treatment modalities.

Exemplary chemotherapeutic agents are vinca alkaloids, epipodophyllotoxins, anthracycline antibiotics, actinomycin D, plicamycin, puromycin, gramicidin D, paclitaxel (TAXOL®, Bristol Myers Squibb), colchicine, cytochalasin B, emetine, maytansine, and amsacrine (or "mAMSA"). The vinca alkaloid class is described in *Goodman and Gilman's The Pharmacological Basis of Therapeutics*, 1277-1280 (7th ed. 1985) (hereafter "Goodman and Gilman"). Exemplary of vinca alkaloids are vincristine, vinblastine, and vindesine. The epipodophyllotoxin class is described in Goodman and Gilman, supra at 1280-1281. Exemplary of epipodophyllotoxins are etoposide, etoposide orthoquinone, and teniposide. The anthracycline antibiotic class is described in Goodman and Gilman, supra at 1283-1285. Exemplary of anthracycline antibiotics are daunorubicin, doxorubicin, mitoxantraone, and bisanthrene. Actinomycin D, also called Dactinomycin, is described in Goodman and Gilman, supra at 1281-1283. Plicamycin, also called mithramycin, is described in Goodman and Gilman, supra at 1287-1288. Additional chemotherapeutic agents include cisplatin (PLATINOL® Bristol Myers Squibb); carboplatin (PARAPLATIN®, Bristol Myers Squibb); mitomycin (MUTAMYCIN®, Bristol Myers Squibb); altretamine (HEXALEN®, U.S. Bioscience, Inc.); cyclophosphamide (CYTOXAN®, Bristol Myers Squibb); lomustine [CCNU] (CEENU®, Bristol Myers Squibb); carmustine [BCNU] (BICNU®, Bristol Myers Squibb); irinotecan (CPT-11).

Methods of administering chemotherapeutic drugs vary depending upon the specific agent used, as would be mown to one skilled in the art. Depending upon the agent used, chemotherapeutic agents may be administered, for example, by injection (intravenously, intramuscularly, intraperitoneally, subcutaneously, intratumor, intrapleural) or orally.

As used herein, the administration of a compound "in conjunction with" a second compound means that the two compounds are administered closely enough in time that the presence of one alters the biological effects of the other. The two compounds may be administered simultaneously (concurrently) or sequentially. Simultaneous administration may be carried out by mixing the compounds prior to administration, or by administering the compounds at the same point in time but at different anatomic sites or using different routes of administration.

The phrases "concurrent administration", "simultaneous administration" or "administered simultaneously" as used herein, means that the compounds are administered at the same point in time or immediately following one another. In the latter case, the two compounds are administered at times sufficiently close that the results observed are essentially indistinguishable from those achieved when the compounds are administered at the same point in time.

Many chemotherapeutic agents act at specific phases of the cell cycle, and are active only against cells in the process of division. Neoplasms which are the most susceptible to chemotherapy are those with a high percentage of cells in the process of division, including but not limited to breast, liver, brain, lung, and ovarian cancer.

Anti-cancer radiotherapy may be carried out in any conventional manner as is known in the art, including external beam radiotherapy and implanted radioactive sources (such as temporarily implanted radioactive iodine sources to deliver high dose local therapy).

Applicants specifically intend that the disclosures of all U.S. patents cited herein be incorporated by reference in their entirety The following examples are provided to illustrate the present invention, and should not be construed as limiting thereof.

Example 1

Expression of Super-Repressor $I_\kappa B_\alpha$ in HT1080I Cells Blocked TNF-Stimulated NF-$_\kappa$B Nuclear Translocation HT1080 fibrosarcoma cells were co-transfected with the pCMV empty vector to produce control cells HT1080V; HT1080, cells co-transfected with the pCMV vector containing a cDNA encoding the super-repressor I$\kappa$B$\alpha$ and with the pCEP4 vector for hygromycin B selection (400 µg/ml) provided HT1080I cells that expressed the super-repressor I$\kappa$B$\alpha$. Transfection was by the lipofectamine protocol (Gibco/BRL. I$\kappa$B$\alpha$ levels were determined by immunoblotting (ECL, Amersham) to equivalent amounts of protein from the different cell lines with an antibody to human I$\kappa$B$\alpha$ (Rockland, Inc., Royertown, Pa.). The expression of super-repressor I$\kappa$B$\alpha$ in HT1080I cells efficiently blocked TNF-stimulated NF-$\kappa$B nuclear translocation as determined by electrophoretic mobility-shift assay (EMSA) (data not shown).

Example 2

Expression of the Super-Repressor $I_\kappa B_\alpha$ Enhances TNF-Mediated Apoptosis HT1080V (open squares) and HT1080I cells (solid diamonds) were treated with TNFα (20 ng/ml) for varying times and surviving cells were quantified by crystal violet assay Mehlen et al., *EMBO J.* 15:2695 (1996)). Data shown (FIG. 1A) are the mean of three independent experiments±SD, and the percentage cell survival was defined as the relative number of TNF treated versus untreated cells. Cell survival was reduced in HT1080I cells compared to HT1080V controls.

TNF-induced apoptosis was detected by TUNEL staining (Graeber et al., *Nature* 379:88 (1996)). HT1080V (V) and HT1080I (I) cells were untreated (−TNF) or stimulated (+TNF) with 50 ng/ml TNFα for 7 hr and fixed with 4% paraformaldehyde. The staining was done according to the manufacturer's instructions (Boehringer Mannheim). HT1080I cells treated with TNF showed the condensed morphology typical of apoptotic cells (FIG. 1B). In the absence of TNF, neither control cells nor super-repressor I$\kappa$B$\alpha$ expressing cells showed apoptotic morphology. In the presence of TNF, only super-repressor I$\kappa$B$\alpha$ expressing cells showed apoptotic morphology, indicating that the presence of I$\kappa$B$\alpha$ enhanced TNFα-induced apoptosis.

Example 3

NF-$_\kappa$B Suppresses TNF-Induced Apoptosis

To exclude the possibility that the expression of the super-repressor form of I$\kappa$B$\alpha$ leads to a function that is different from the inhibition of NF-$\kappa$B, the requirement for NF-$\kappa$B in the inhibition of TNF-induced apoptosis was confirmed. Cells were pre-treated with interleukin-1 (IL-1), an activator of NF-$\kappa$B that does not initiate apoptosis, prior to combined cycloheximide (CHX) and TNF treatment.

HT1080V and HT1080I cells were preincubated with 10 ng/ml IL-1β (R & D Systems) for 5 hours (+Pre IL-1), or were left untreated. Cells were then treated with 10 µg/ml cycloheximide (CHX) and different concentrations of TNFα (0-50 ng/ml). Surviving cells were quantified by crystal violet assay (Mehlen et al., *EMBO J.* 15:2695 (1996)). As shown in FIG. 2A, Interleukin-1 (IL-1) pre-treatment inhibited TNFα+CHX-induced apoptosis in HT1080V cells. Open squares represent HT1080V cells without IL-1 pretreatment; closed squares represent HT1080V cells pretreated with IL-1; circles represent HT1080I cells without IL-1 pretreatment; triangles represent HT1080I cells pretreated with IL-1.

Example 4

Proteasome Inhibitors Enhanced TNF Apoptosis

The effect of a proteasome inhibitor on TNF-treated cells was investigated. Proteasome inhibitors of the peptide aldehyde category are potent inhibitors of NF-$\kappa$B activation (Palombello et al., *Cell* 78:773 (1994); Chen et al., *Genes Dev.* 9:1586(1995)). It was demonstrated that, in a dose-dependent fashion, the proteasome inhibitor MG132 (Z-leu-leu-leu-H) strongly enhanced TNF-induced killing of HT1080V cells (data not shown). Cell viability experiments were used to monitor the effectiveness of MG132 in enhancing TNF-induced cell killing.

Example 5

Restoration of Resistance to TNF Apoptosis by NF-$_\kappa$B

Expression of the p50 and RelA/p65 NF-$\kappa$B subunits restored cell resistance to TNP killing in cells expressing the super-repressor I$\kappa$B. HT1080I cells (expressing the super-repressor I$\kappa$B$\alpha$) were either co-transfected with pcDNA3-LacZ (Invitrogen) and pCMV-p65 (2 µg) and pCMV-p50 (2 µg) (hatched bars); or with the LacZ and empty vectors. Transfection was by the lipofectamine protocol, After 40 hours, cells were treated with different concentrations of TNFα for an additional 24 hours. The results are from the mean±SD of two experiments.

As shown in FIG. 2B, cell survival after exposure to TNFα was increased in cells expressing the NF-$\kappa$B subunits, compared to control cells.

Example 6

Ionizing Radiation and Daunorubicin Induce Nuclear Translocation of NF-$\kappa$B in Control Cells Daunorubicin and ionizing radiation induce nuclear translocation of NF-$\kappa$B. HT1080V (V) and HT1080I (I) cells were treated with 1 µM daunorubicin (Sigma), 50 nM staurosporine (Sigma), or were irradiated (5 Gy) for the indicated times. EMSA was performed as previously described (Finco et al., *Proc. Natl. Acad. Sci. USA*, 91:11884 (1994) to assess nuclear translocation of NF-κB. Results of EMSA are provided in FIG. 3A, where lanes 1-5=daunorubicin treatment; lanes 6-9=staurosporine treatment; and lanes 10-13, ionizing radiation treatment.

As shown in FIG. 3A, after six hours, only slight nuclear translocation of NF-κB was evident in control (HT1080V) cells treated with staurosporine (lanes 6-9). In control cells treated with daunorubicin (lanes 1-3), translocation was clearly evident at five hours post-treatment; no translocation was evident in super-repressor IκBα expressing cells treated with daunorubicin (lanes 4-5). In control cells treated with ionizing radiation (lanes 10-11), translocation was clearly evident at five hours post-treatment; no translocation was evident in super-repressor IκBα expressing cells treated with ionizing radiation (lanes 12-13).

Example 7

Figure 3B:
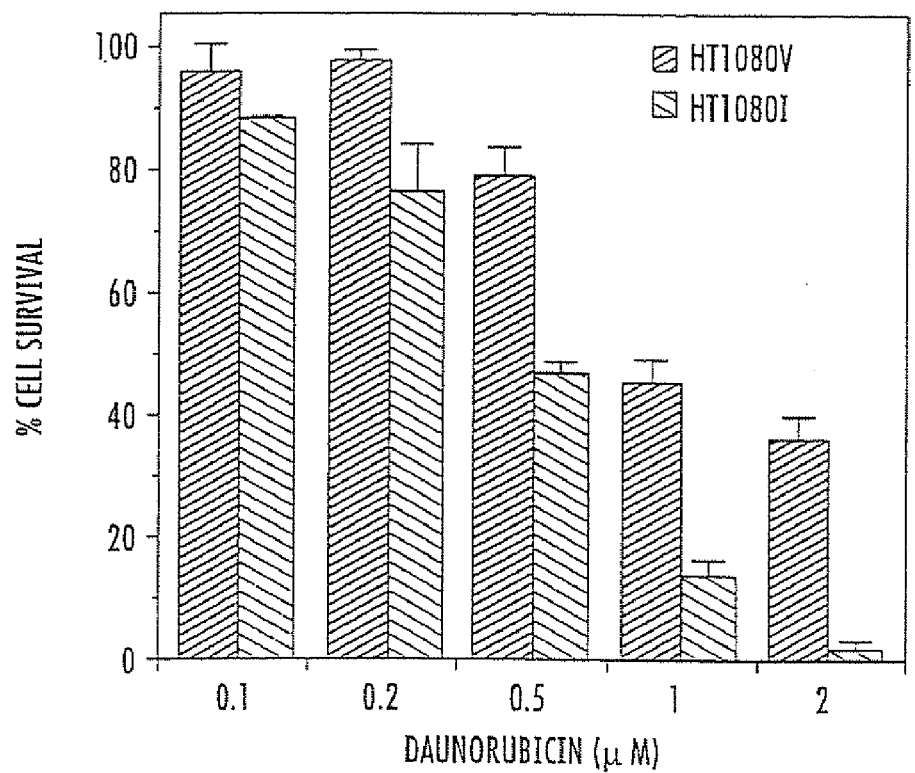
FIG. 3B compares cell survival of HT1080V cells (control; solid bars) and HT1080I cells (expressing the super-repressor IκBα; hatched bars) treated with varying concentrations of daunorubicin for 24 hours. (Results are from the mean of four separate experiments). The overexpression of super-repressor IκBα enhanced cell killing by daunorubicin.

Overexpression of $I_\kappa B_\alpha$ Enhanced Cell-Killing by Ionizing Radiation and Daunorubicin As indicated in FIG. 3B, HT1080V cells and HT1080I cells (hatched bars) were treated with the varying concentrations of daunorubicin (0.1 to 2.0 µM) for 24 hours. Surviving cells were quantified by crystal violet assay (Mehlen et al., *EMBO J.* 15:2695 (1996). Data shown represent the mean of four separate experiments. Cell survival over time was reduced in HT1080I cells in response to daunorubicin, compared to control cells.

Figure 3C:
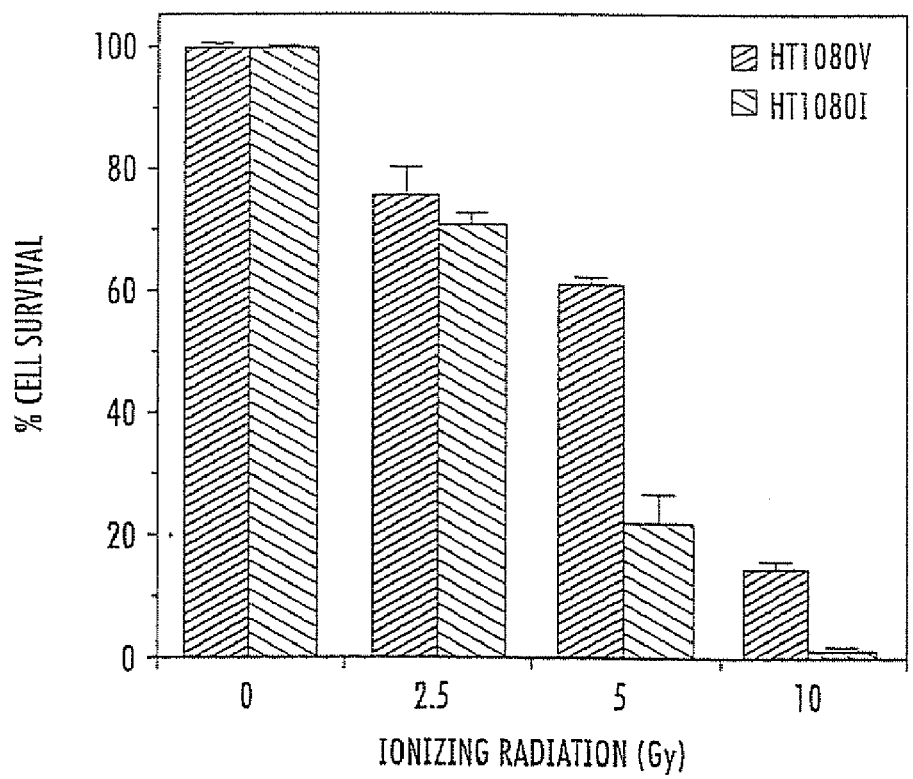
FIG. 3C compares cell survival of HT1080V cells (control; solid bars) and HT1080I cells (expressing the super-repressor IκBα; hatched bars) 14 days after treatment with ionizing radiation for the indicated doses (Gy). (Results shown represent three independent experiments and are expressed as the mean±SD). The overexpression of super-repressor IκBα enhanced cell killing by ionizing radiation.

Five hundred HT1080V cells and 500 HT1080I cells were plated in separate six-well plates. Twenty-four hours later the cells were exposed to ionizing radiation in doses from 0 Gy to 10 Gy, and fourteen days later cell clones were counted. Each group was performed in triplicate. Results are shown in FIG. 3C and represent three independent experiments expressed as the mean±SD. At radiation doses of 5 Gy and 10 Gy, cell survival was reduced in HT1080I cells compared to control HT1080V cells.

The above results indicate that the overexpression of super-repressor IκBα in HT1080I cells enhanced cell killing by daunorubicin and ionizing radiation.

Example 8

Augmentation of Cytotoxicity of Vincristine by NF-κB Inhibition

The present inventors' preliminary data additionally indicate that cell killing by vincristine is augmented by the inhibition of NF-κB (data not shown). HT1080V and HT1080I cells were treated with; vincristine and cell viability was determined. Cell killing in HT1080I cells was enhanced compared to that in HT1080V cells.

Example 9

Adenoviral Delivery of the Super-Repressor $I_\kappa B$ Enhances CPT-11 Efficacy The antineoplastic agent CPT-11 (irinotecan) was determined to activate NF-κB (data not shown). The co-administration of the super-repressor IκB with CPT-11 was investigated in nude mice with experimentally induced fibrosarcomas. Delivery of the super-repressor IκB was achieved by injecting tumors directly with an adenovirus encoding the super-repressor IκB under the control of the cytomegalovirus (CMV) promoter. A control adenoviral vector contained the CMV promoter but not the coding sequence for IκB. Animals were systemically treated with CPT-11, according to protocols known in the art.

Figure 4:
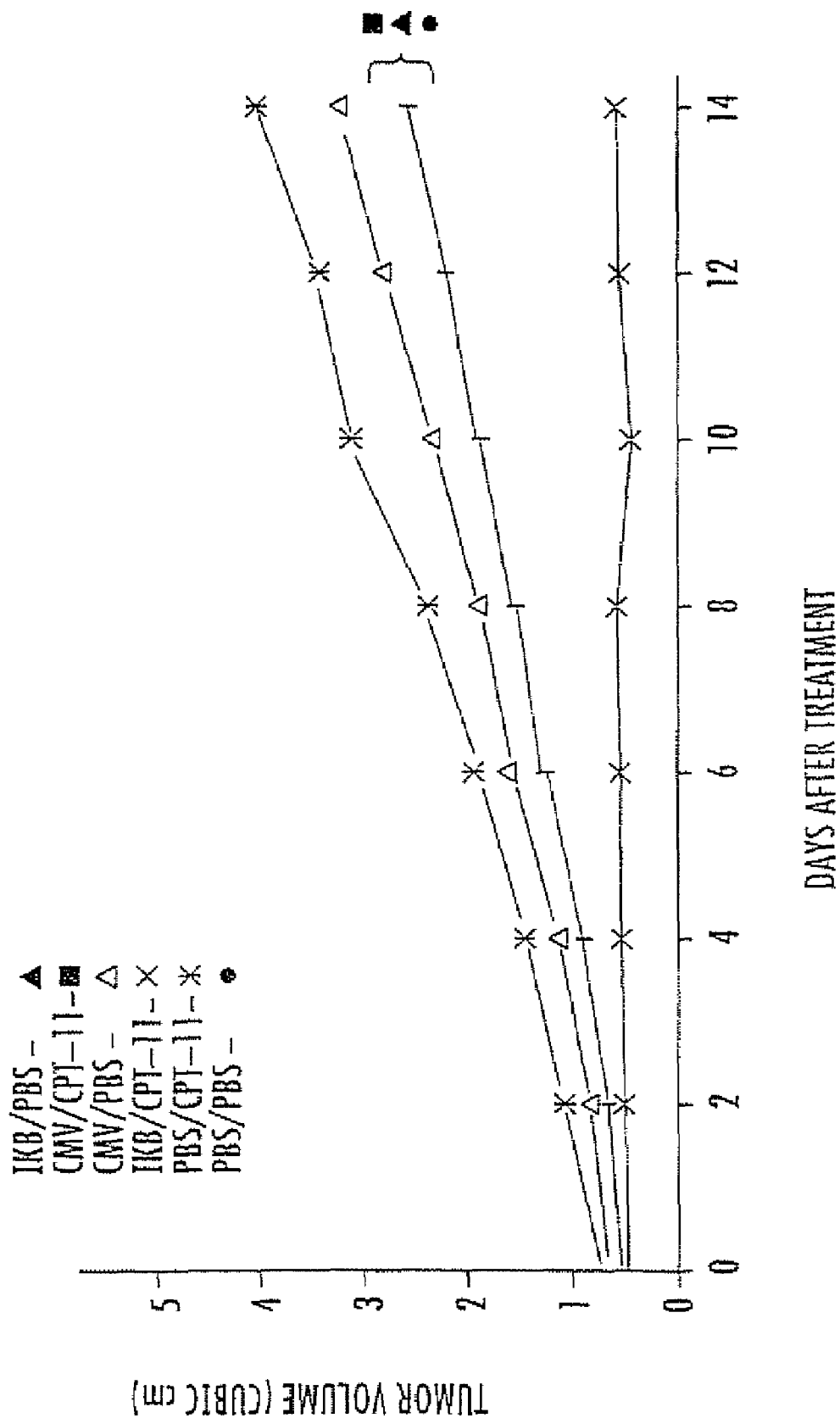
FIG. 4 graphs tumor growth in mice after treatment with the antineoplastic CPT-11 (irinotecan), with and without the adenoviral delivery of the super-repressor IκB. Tumors receiving both IκB and CPT-11 showed essentially no growth during the 20 days after treatment.

Treatments were as indicated in FIG. 4, where solid triangles indicate IκB and PBS treatment; solid squares indicate treatment with the control viral vector (CMV) and CPT-11; closed circles indicate treatment with PBS only; open triangles indicate treatment with the control viral vector and PBS; crosses (X's) indicate treatment with IκB and CPT-11; and asterisks indicate treatment with PBS and CPT-11. (The data points for IκB and PBS treatment (solid triangles), CMV and CPT-11 treatment (solid squares), and PBS treatment (closed circles) were so similar that they are indicated as a single line on FIG. 4.)

As shown in FIG. 4, growth of fibrosarcoma tumors in mice was reduced by co-administration of super-repressor IκB and CPT-11 (bottom line on graph, indicated by X's), compared to tumor growth in animals treated with CPT-11 alone (top line, indicated by asterisks). Tumors receiving both IκB and CPT-11 showed essentially no growth during the 20 days after treatment. CPT-induced cell death was by apoptosis (data not shown).

The above results indicate that the efficacy of anti-neoplastic therapies can be enhanced by the concomitant suppression of NF-κB activation.

That which is claimed:

1. A method of enhancing the cytotoxic effects of an antineoplastic chemotherapeutic agent, comprising administering to a mammalian subject in need of said antineoplastic chemotherapeutic agent a therapeutically effective amount of Nuclear Factor-kappa B (NF-κB) inhibitor in conjunction with the administration of a dosage of the chemotherapeutic agent, whereby the cytotoxic effect of said antineoplastic chemotherapeutic agent is increased compared to that which would occur in the absence of NF-κB inhibitor;
   wherein the dosage of said antineoplastic chemotherapeutic agent is decreased as compared to a dosage effective without administering the NF-κB inhibitor in conjunction with the administration of the chemotherapeutic agent,
   and wherein said subject is afflicted with lung, breast, prostate, brain, kidney, liver, spleen, pancreas, bone or muscle cancer, leukemia or lymphoma, a sarcoma, a carcinoma or a mixed tumor.

2. The method according to claim 1 wherein said NF-κB inhibitor is administered simultaneously with said chemotherapeutic agent.

3. The method of claim 1 where said chemotherapeutic agent is selected from the group consisting of vinca alkaloids, epipodophyllotoxins, anthracyclene antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, carmustine, and irinotecan.

4. The method according to claim 1, wherein said subject is afflicted with lung, breast, prostate, brain, kidney, liver, spleen, pancreas, bone or muscle cancer.

5. The method according to claim 1, wherein said subject is afflicted with leukemia or lymphoma.

6. The method according to claim 1, wherein said subject is afflicted with a sarcoma, a carcinoma or a mixed tumor.

7. The method according to claim 1, wherein said NF-κB inhibitor and said chemotherapeutic agent are administered sequentially.

8. The method of enhancing the cytotoxic effects of an antineoplastic chemotherapeutic agent, comprising administering to a mammalian subject in need of said antineoplastic chemotherapeutic agent a therapeutically effective amount of Nuclear Factor-kappa B (NF-κB) inhibitor in conjunction with the administration of a dosage of the chemotherapeutic agent, whereby the cytotoxic effect of said antineoplastic chemotherapeutic agent is increased compared to that which would occur in the absence of NF-κB inhibitor;
  wherein the dosage of said antineoplastic chemotherapeutic agent is decreased as compared to a dosage effective without administering the NF-κB inhibitor in conjunction with the administration of the chemotherapeutic agent,
  wherein said NF-κB inhibitor is selected from the group consisting of: a proteasome inhibitor, an inhibitor of ubiquitin conjugation, an inhibitor of proteasome peptidases, and a protease inhibitor.

9. The method according to claim 8 wherein said NF-κB inhibitor is administered simultaneously with said chemotherapeutic agent.

10. The method of claim 8 where said chemotherapeutic agent is selected from the group consisting of vinca alkaloids, epipodophyllotoxins, anthracyclene antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, carmustine, and irinotecan.

11. The method according to claim 8, wherein said subject is afflicted with lung, breast, prostate, brain, kidney, liver, spleen, pancreas, bone or muscle cancer.

12. The method according to claim 8, wherein said subject is afflicted with leukemia or lymphoma.

13. The method according to claim 8, wherein said subject is afflicted with a sarcoma, a carcinoma or a mixed tumor.

14. The method according to claim 8, wherein said NF-κB inhibitor and said chemotherapeutic agent are administered sequentially.

15. The method according to claim 1, wherein said subject is afflicted with breast cancer.

16. The method according to claim 15, wherein said chemotherapeutic agent is selected from the group consisting of cisplatin, carboplatin, irinotecan, paclitaxel, vinca alkaloids, and cyclophosphamide.

17. The method according to claim 1, wherein said subject is afflicted with lung cancer.

18. The method according to claim 17, wherein said chemotherapeutic agent is selected from the group consisting of cisplatin, carboplatin, irinotecan, paclitaxel, vinca alkaloids, and cyclophosphamide.

19. The method according to claim 1, wherein said subject is afflicted with prostate cancer.

20. The method according to claim 19, wherein said chemotherapeutic agent is selected from the group consisting of cisplatin, carboplatin, irinotecan, paclitaxel, vinca alkaloids, and cyclophosphamide.

21. The method according to claim 1, wherein said subject is afflicted with brain cancer.

22. The method according to claim 21, wherein said chemotherapeutic agent is selected from the group consisting of cisplatin, carboplatin, irinotecan, paclitaxel, vinca alkaloids, and cyclophosphamide.

* * * * *

UNITED STATES PATENT AND TRADEMARK OFFICE
CERTIFICATE OF CORRECTION

| | | |
|---|---|---|
| PATENT NO. | : 7,700,545 B2 | Page 1 of 1 |
| APPLICATION NO. | : 11/535720 | |
| DATED | : April 20, 2010 | |
| INVENTOR(S) | : Baldwin et al. | |

It is certified that error appears in the above-identified patent and that said Letters Patent is hereby corrected as shown below:

On Title Page:
Item 63, Related U.S. Application Data: Please correct "10/979,402"
to read -- 10/979,403 --

Signed and Sealed this

Twenty-first Day of September, 2010

David J. Kappos
*Director of the United States Patent and Trademark Office*